United States Patent
Monari et al.

(10) Patent No.: US 8,778,402 B2
(45) Date of Patent: Jul. 15, 2014

(54) DRY POWDER FORMULATION COMPRISING A CORTICOSTEROID AND A BETA-ADRENERGIC FOR ADMINISTRATION BY INHALATION

(71) Applicant: Chiesi Farmaceutici S.p.A., Parma (IT)

(72) Inventors: Elisa Monari, Parma (IT); Anna Maria Cantarelli, Parma (IT); Daniela Cocconi, Parma (IT); Irene Pasquali, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/748,882

(22) Filed: Jan. 24, 2013

(65) Prior Publication Data
US 2013/0189324 A1    Jul. 25, 2013

(30) Foreign Application Priority Data
Jan. 25, 2012  (EP) .................... 12152392

(51) Int. Cl.
*A61K 9/14*  (2006.01)
*A61K 9/16*  (2006.01)
*A61K 9/50*  (2006.01)
*C07J 73/00*  (2006.01)

(52) U.S. Cl.
USPC .............. 424/489; 514/171; 514/630; 540/63

(58) Field of Classification Search
None
See application file for complete search history.

(56) References Cited

U.S. PATENT DOCUMENTS

| 6,645,466 | B1 | 11/2003 | Keller et al. |
| 2007/0202053 | A1* | 8/2007 | Bilzi et al. ....................... 424/46 |
| 2010/0055192 | A1* | 3/2010 | Musa et al. .................... 424/489 |
| 2010/0269825 | A1* | 10/2010 | Cocconi et al. .......... 128/203.15 |
| 2011/0033544 | A1* | 2/2011 | Nagata et al. ................. 424/489 |

FOREIGN PATENT DOCUMENTS

| EP | 1 312 357 | 5/2003 |
| EP | 1 944 018 | 7/2008 |
| EP | 1 982 709 | 10/2008 |
| WO | 01/78693 | 10/2001 |
| WO | 02/28377 | 4/2002 |
| WO | 2011/018532 | 2/2011 |
| WO | 2011/120779 | 10/2011 |
| WO | 2011/131663 | 10/2011 |

OTHER PUBLICATIONS

European Search Report in Application No. 12152392.2, issued May 23, 2012.
Guchardi R et al., International Journal of Pharmaceutics, vol. 348, No. 1-2 (2007) pp. 10-17.

* cited by examiner

*Primary Examiner* — Frederick Krass
*Assistant Examiner* — Isaac Shomer
(74) *Attorney, Agent, or Firm* — Oblon, Spivak, McClelland, Maier & Neustadt, L.L.P.

(57) ABSTRACT

Dry powder formulations comprising a corticosteroid and a $beta_2$-adrenergic drug in combination are useful for the prevention and/or treatment of inflammatory or obstructive airways diseases.

21 Claims, No Drawings

DRY POWDER FORMULATION COMPRISING A CORTICOSTEROID AND A BETA-ADRENERGIC FOR ADMINISTRATION BY INHALATION

CROSS-REFERENCES TO RELATED APPLICATIONS

This application claims priority to European Patent Application No. 12152392.2, filed on Jan. 25, 2012, which is incorporated herein by reference in its entirety.

BACKGROUND OF THE INVENTION

1. Field of the Invention

The present invention relates to formulations for administration by inhalation by means of dry powder inhalers. In particular, the present invention relates to dry powder formulations comprising a corticosteroid and a $beta_2$-adrenergic drug in combination, its process of preparation, and therapeutic uses thereof.

2. Discussion of the Background

Active substances commonly delivered by inhalation include bronchodilators such as beta-2 adrenoreceptor agonists and anticholinergics, corticosteroids, anti-allergics, and other active ingredients that may be efficiently administered by inhalation, thus increasing the therapeutic index and reducing side effects of the active material.

Formoterol, i.e. 2'-hydroxy-5'-[(RS)-1-hydroxy-2{[(RS)-p-methoxy-α-methylphenethyl]amino}ethyl]formanilide, particularly its fumarate salt (hereinafter indicated as FF), is a well known beta-2 adrenergic receptor agonist, currently used clinically in the treatment of bronchial asthma, chronic obstructive pulmonary disease (COPD) and related disorders.

Beclometasone dipropionate (BDP) is a potent anti-inflammatory steroid, named (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate, available under a wide number of brands for the prophylaxis and/or treatment of inflammatory respiratory disorders.

A formulation for pressurized metered dose inhalers (pMDIs) containing both active ingredients in combination, both dissolved in a mixture of HFA134a and ethanol as co-solvent is currently on the market. It has been quoted in the literature as FF/BDP extra-fine formulation.

Said formulation provides a high lung deposition and uniform distribution throughout the bronchial tree, and is characterized by the fact that is capable of delivering a high fraction of particles having a diameter equal or less than 1.1 microns. In particular, upon actuation of the inhaler, it gives rise to a respirable fraction of about 40% and a fraction of particles having a diameter equal or less than 1.1 microns of about 12% for both active ingredients.

The major advantage of said formulation is related to the improved penetration into the bronchiole-alveolar distal part of the respiratory tree wherein inflammation is known to play a role in spontaneous exacerbations of asthma symptoms and wherein it is known that the density of the beta-2 adrenergic receptors is particularly high. However, despite their popularity, pMDI formulations may have some disadvantages in particular in elderly and pediatric patients, mostly due to their difficulty to synchronize actuation from the device with inspiration.

Dry powder inhalers (DPIs) constitute a valid alternative to MDIs for the administration of drugs to airways. On the other hand, drugs intended for inhalation as dry powders should be used in the form of micronized particles. Their volumetric contribution could represent an obstacle in the design of a formulation therapeutically equivalent to one wherein the drugs are delivered in form of liquid droplets.

WO 01/78693, which is incorporated herein by reference in its entirety, discloses a dry powder formulation comprising formoterol and BDP in combination as active ingredients and, as a carrier, a fraction of coarse particles and a fraction made of fine excipient particles and magnesium stearate. Upon its actuation, the respirable fraction of BDP is about 40%, while that of formoterol is about 47%.

More recently Mariotti et al. (European Respiratory Society Annual Congress held in Amsterdam on Sep. 24-28, 2011), presented data about a FF/BDP dry powder formulation having a respirable fraction of about 70% for both active ingredients.

However, there remains a need for improved formulations, for administration by inhalation by means of dry powder inhalers, which contain a corticosteroid and a $beta_2$-adrenergic drug in combination

SUMMARY OF THE INVENTION

Accordingly, it is one object of the present invention to provide novel powder formulation for DPIs comprising formoterol fumarate and BDP in combination.

It is another object of the present invention to provide novel methods of preparing such formulation.

It is another object of the present invention to provide novel methods of treating and/or preventing certain diseases by administering such a formulation.

These and other objects, which will become apparent during the following detailed description, have been achieved by the inventors' discovery that dry powder formulations for use in a dry powder inhaler (DPI) comprising:

(a) a fraction of fine particles made of a mixture composed of 90 to 99.5 percent by weight of particles of a physiologically acceptable excipient and 0.5 to 10 percent by weight of magnesium stearate, said mixture having a mass median diameter lower than 20 micron;

(b) a fraction of coarse particles constituted of a physiologically acceptable excipient having a mass median diameter equal to or higher than 100 micron, wherein the ratio between the fine particles and the coarse particles being between 1:99 and 30:70 percent by weight; and (c) formoterol fumarate dihydrate in combination with beclometasone dipropionate (BDP) as active ingredient both in form of micronized particles;

wherein i) no more than 10% of said BDP particles have a diameter lower than 0.6 microns, ii) no more than 50% of said particles have a diameter comprised between 1.5 microns and 2.0 microns; and iii) at least 90% of said particles have a diameter lower than 4.7 microns overcome the problems indicated above and in particular provide a powder formulation having therapeutic characteristics matching those of the corresponding pMDI formulation in form of solution.

Thus, in a first aspect, the present invention provides dry powder formulations for use in a dry powder inhaler (DPI) comprising:

(a) a fraction of fine particles made of a mixture composed of 90 to 99.5 percent by weight of particles of a physiologically acceptable excipient and 0.5 to 10 percent by weight of magnesium stearate, said mixture having a mass median diameter lower than 20 micron;

(b) a fraction of coarse particles constituted of a physiologically acceptable excipient having a mass median diameter equal to or higher than 100 micron, wherein the ratio between the fine particles and the coarse particles being between 1:99 and 30:70 percent by weight; and (c) formoterol fumarate dihydrate in combination with beclometasone dipropionate (BDP) as active ingredient both in form of micronized particles;

wherein i) no more than 10% of said BDP particles have a diameter lower than 0.6 microns, ii) no more than 50% of said particles have a diameter comprised between 1.5 microns and 2.0 microns; and iii) at least 90% of said particles have a diameter lower than 4.7 microns In a second aspect, the present invention provides a process for preparing such a dry powder formulation of the invention comprising the step of mixing the carrier particles with the active ingredients.

In a third aspect, the present invention provides a dry powder inhaler filled with the above dry powder formulation.

In a fourth aspect, the present invention provides such a formulation for use in the prevention and/or treatment of an inflammatory or obstructive airways disease such as asthma or chronic obstructive pulmonary disease (COPD).

In a fifth aspect, the present invention provides a method of preventing and/or treating an inflammatory or obstructive airways disease such as asthma or chronic obstructive pulmonary disease (COPD), which comprises administering by inhalation an effective amount of the formulation of the invention.

In a sixth aspect, the present invention provides the use of such a formulation in the manufacture of a medicament for the prevention and/or treatment of an inflammatory or obstructive airways disease such as asthma or chronic obstructive pulmonary disease (COPD).

DETAILED DESCRIPTION OF THE PREFERRED EMBODIMENTS

By the term "physiologically acceptable" it is meant a safe pharmacologically-inert substance.

By "daily therapeutically effective dose" it is meant the quantity of active ingredient administered by inhalation upon actuation of the inhaler.

Said daily dose may be delivered in one or more actuations (shots or puffs) of the inhaler.

By the term "fine particles" it is meant particles having a size up to few tenths of microns.

By the term "micronized" it is meant a substance having a size of few microns.

By the term "coarse" it is meant particles having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients is expressed in terms of volume diameter, while that of the excipient is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values: i) the volume median diameter d(v,0.5) which is the volume diameter where 50% of the distribution is above and 50% is below; ii) d(v,0.9), where 90% of the volume distribution is below this value; iii) d(v, 0.1), where 10% of the volume distribution is below this value. The span is the width of the distribution based on the 10%, 50% and 90% quantile and is calculated according to the formula.

$$\text{Span} = \frac{D[v, 0.9] - D[v, 0.1]}{D[v, 0.5]}$$

Upon aerosolization, the particle size is expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able to ensure an accurate and reproducible delivering of the therapeutically effective dose.

Flow characteristics can be evaluated by different tests such as angle of repose, Carr's index, Hausner ratio or flow rate through an orifice.

In the context of the present application the flow properties were tested by measuring the flow rate through an orifice according to the method described in the European Pharmacopeia (Eur. Ph.) 7.3, $7^{th}$ Edition, which is incorporated herein by reference in its entirety.

The expression "good homogeneity" refers to a formulation wherein, upon mixing, the uniformity of distribution of the active ingredient, expressed as coefficient of variation (CV) also known as relative standard deviation (RSD), is less than 2.5%, preferably equal to or less than 1.5%.

The expression "respirable fraction" refers to an index of the percentage of active particles which would reach the deep lungs in a patient.

The respirable fraction, also termed fine particle fraction (FPF), is evaluated using a suitable in vitro apparatus such as Andersen Cascade Impactor (ACI), Multi Stage Liquid Impinger (MLSI) or Next Generation Impactor (NGI), preferably by ACI, according to procedures reported in common Pharmacopoeias, in particular in the European Pharmacopeia (Eur. Ph.) 7.3, $7^{th}$ Edition, which is incorporated herein by reference in its entirety.

It is calculated by the percentage ratio between the fine particle mass (formerly fine particle dose) and the delivered dose.

The delivered dose is calculated from the cumulative deposition in the apparatus, while the fine particle mass is calculated from the deposition of particles having a diameter<5.0 micron.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

The term "coating" refers to the covering of the surface of the excipient particles by forming a thin film of magnesium stearate around said particles.

The present invention is directed to a dry powder formulation for use in a dry powder inhaler (DPI) comprising a fraction of fine particles (a), a fraction of coarse particles (b), and formoterol fumarate (FF) dihydrate in combination with beclometasone dipropionate (BDP) as active ingredients, having the characteristics disclosed herein.

The fractions (a) and (b) constitute the "carrier" particles.

It has been surprisingly found that in order to obtain a FF/BDP dry powder formulation therapeutically equivalent to the corresponding pMDI formulation currently on the market, it is necessary to generate a higher respirable fraction (FPF) as well as a higher fraction of particles having a diameter equal or less than 1.1 microns, for both active ingredients.

It has also been found that this can be achieved by strictly controlling the particle size of the micronized BDP, and preferably its specific surface area.

Unexpectedly, it has been indeed further found that by setting the particle size distribution of BDP to the values herein claimed, not only its respirable fraction increases, but also that of formoterol fumarate (more than 60% vs about 47%).

Furthermore, the use of a micronized BDP characterized by such a selected, narrow, and well defined particle size distribution allows a better reproducibility of its fine particle fraction (FPF) during repeated administration.

The formulations according to the present invention also show a good homogeneity of the active ingredients, a good flowability, and adequate physical and chemical stability in the inhaler before use for pharmaceutical purposes.

Advantageously, the fine and coarse excipient particles may be constituted of any physiologically acceptable material or combination thereof; preferred excipients are those made of crystalline sugars, in particular lactose; the most preferred are those made of α-lactose monohydrate.

Preferably, the coarse excipient particles and the fine excipient particles are both constituted of α-lactose monohydrate.

The fraction of fine particles (a) must have a mass median diameter (MMD) lower than 20 microns, advantageously equal to or lower than 15 microns, preferably equal to lower than 10 microns, even more preferably equal to or lower than 6 microns.

Advantageously, the mass diameter of 90% of the fine particles (a) is lower than 35 microns, more advantageously lower than 25 microns, preferably lower than 15 microns, even more preferably lower than 10 microns.

The ratio between the excipient particles and magnesium stearate within the fraction (a) may vary depending on the doses of the active ingredients.

Advantageously, said fraction is composed of 90 to 99.5% by weight of the excipient and 0.5 to 10% by weight of magnesium stearate, preferably of 95 to 99% of the excipient, and 1 to 5% of magnesium stearate. A preferred ratio is 98% of the excipient and 2% of magnesium stearate.

Advantageously, at least 90% by weight of the particles of magnesium stearate has a starting mass diameter of not more than 35 microns and a MMD of not more than 15 microns, preferably not more than 10 microns.

Advantageously, magnesium stearate may coat the surface of the excipient particles in such a way that the extent of the surface coating is at least of 5%, preferably more than 10%, more preferably more than 15%, even more preferably equal to or more than 35%.

When the excipient particles are made of lactose, the extent of surface coating, which indicates the percentage of the total surface of the excipient particles coated by magnesium stearate, may be determined by water contact angle measurement, and then by applying the equation known in the literature as Cassie and Baxter, cited at page 338 of Colombo I et al *Il Farmaco* 1984, 39(10), 328-341 (which is incorporated herein by reference in it is entirety) and reported below.

$$\cos \partial_{mixture} = f_{Mgst} \cos \partial_{Mgst} + f_{lactose} \cos \partial_{lactose}$$

where:

$f_{Mgst}$ and $f_{lactore}$ are the surface area fractions of magnesium stearate and of lactose, respectively;

$\partial_{MgSt}$ is the water contact angle of magnesium stearate;

$\partial_{lactose}$ is the water contact angle of lactose; and $\partial_{mixture}$ is the experimental contact angle value.

For the purpose of the present invention, the contact angle may be determined with methods that are essentially based on a goniometric measurement. These imply the direct observation of the angle formed between the solid substrate and the liquid under testing. It is therefore quite simple to carry out, being the only limitation related to possible bias stemming from intra-operator variability. It should be, however, underlined that this drawback can be overcome by adoption of a fully automated procedure, such as a computer assisted image analysis. A particularly useful approach is the sessile or static drop method which is typically carried out by depositing a liquid drop onto the surface of the powder in form of disc obtained by compaction (compressed powder disc method).

The extent to which the magnesium stearate coats the surface of the excipient particles may also be determined by scanning electron microscopy (SEM), a well known versatile analytical technique.

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of the excipient particles.

SEM may alternatively be combined with IR or Raman spectroscopy for determining the extent of coating, according to known procedures.

Another analytical technique that may advantageously be used is X-ray photoelectron spectroscopy (XPS), by which it has been possible to calculate both the extent of coating and the depth of the magnesium sterate film around the excipient particles.

The fraction of fine particles (a) may be prepared according to one of the methods disclosed in WO 01/78693, which is incorporated herein by reference in its entirety. Preferably, it could be prepared by co-micronization, more preferably using a ball mill. In some cases, co-milling for at least two hours may be found advantageous, although it will be appreciated that the time of treatment will generally depend on the starting particle size of the excipient particles and the desired size reduction to be obtained.

In a preferred embodiment of the invention the particles are co-micronized starting from excipient particles having a mass diameter less than 250 microns and magnesium stearate particles having a mass diameter less than 35 microns using a jet mill, preferably in inert atmosphere, for example under nitrogen.

As an example, alpha-lactose monohydrate commercially available such as Meggle D 30 or Spherolac 100 (Meggle, Wasserburg, Germany) could be used as starting excipient.

Optionally, the fraction of fine particles (a) may be subjected to a conditioning step according to the conditions disclosed in the pending application n. WO 2011/131663, which is incorporated herein by reference in its entirety.

The coarse excipient particles of the fraction (b) must have a MMD of at least 100 microns, preferably greater than 125 microns, more preferably equal to or greater than 150 microns, even more preferably equal to or greater than 175 microns.

Advantageously, all the coarse particles have a mass diameter in the range 50 to 1000 microns, preferably 60 to 500 microns.

In certain embodiments of the present invention, the mass diameter of said coarse particles might be 80 to 200 microns, preferably 90 to 150 microns, while in another embodiment, the mass diameter might be 200 to 400 microns, preferably 210 to 355 microns.

In a preferred embodiment of the present invention, the mass diameter of the coarse particles is 210 to 355 microns.

In general, the person skilled in the art shall select the most proper size of the coarse excipient particles by sieving, using a proper classifier.

When the mass diameter of the coarse particles is 200 to 400 microns, the coarse excipient particles preferably have a relatively highly fissured surface, that is, on which there are clefts and valleys and other recessed regions, referred to herein collectively as fissures. The "relatively highly fissured" coarse particles can be defined in terms of fissure index or rugosity coefficient as described in WO 01/78695 and WO 01/78693, both of which are incorporated herein by reference in their entireties, and they can be characterized according to the description therein reported. Said coarse particles may also be characterized in terms of tapped density or total intrusion volume measured as reported in WO 01/78695, which is incorporated herein by reference in its entirety.

The tapped density of said coarse particles is advantageously less than 0.8 g/cm$^3$, preferably 0.8 to 0.5 g/cm$^3$. The total intrusion volume is at least 0.8 cm$^3$ preferably at least 0.9 cm$^3$.

The weight ratio between the fraction of fine particles (a) and the fraction of coarse particles (b) is 1:99 to 30:70% by weight, preferably 2:98 to 20:80% by weight. In a preferred embodiment, the ratio is 10:90 to 15:85% by weight, even more preferably is of 10:90 by weight.

The step of mixing the coarse excipient particles (b) and the fine particles (a) is typically carried out in a suitable mixer, e.g. tumbler mixers such as Turbula™, rotary mixers or instant mixer such as Diosna™ for at least 5 minutes, preferably for at least 30 minutes, more preferably for at least two hours. In a general way, the person skilled in the art shall adjust the time of mixing and the speed of rotation of the mixer to obtain a homogenous mixture.

When spheronized coarse excipient particles are desired in order to obtain hard-pellets according to the definition reported above, the step of mixing shall be typically carried out for at least four hours.

All the micronized particles of beclometasone dipropionate (BDP) are characterized by a selected, narrow, and well defined particle size distribution in such a way that: i) no more than 10% of said particles have a diameter lower than 0.6 microns, preferably equal to or lower than 0.7 microns; ii) no more than 50% of said particles have a diameter of 1.5 microns to 2.0 microns, preferably 1.6 to 1.9 microns; and iii) at least 90% of said particles have a diameter equal to or lower than 4.7 microns, preferably equal to or lower than 4.0 microns, more preferably equal to or lower than 3.8 microns.

The particular size distribution of BDP is characterized by: a d(v0.1) of 0.8 to 1.0 micron, preferably 0.85 to 0.95 microns; a d(v0.5) of 1.5 to 2.0 microns preferably 1.6 and 1.9 microns, a d(v0.9) of 2.5 to 4.7 microns, preferably 3.0 to 4.0 microns.

However the width of the particle size distribution of said BDP particles, expressed as a span, should be 1.2 to 2.2, preferably 1.3 to 2.1, more preferably 1.6 to 2.0, according the Chew et al J Pharm Pharmceut Sci 2002, 5, 162-168, which is incorporated herein by reference in its entirety. The span corresponds to [d(v,0.9)−d(v,0.1)]/d(v,0.5).

Advantageously, at least 99% of said particles [d(v,0.99)] have a diameter equal to or lower than 6.0 microns, and substantially all the particles have a volume diameter of 6.0 to 0.4 microns, preferably 5.5 to 0.45 microns.

The size of the particles of the active is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

Advantageously, the micronized particles of BDP have also a specific surface area of 5.5 to 7.0 m$^2$/g, preferably 5.9 to 6.8 m$^2$/g. The Specific Surface Area is determined by Brunauer-Emmett-Teller (BET) nitrogen adsorption method according to a procedure known in the art.

All the micronized particles of formoterol fumarate dihydrate may have a diameter of less than 10 microns, preferably less than 6 microns. Advantageously at least 90% of the particles have a volume diameter lower than 5.0 micron. In a particular embodiment, the particle size distribution is such that: i) no more than 10% of the particles have a volume diameter lower than 0.8 microns, ii) no more than 50% of particles have a volume diameter lower than 1.7 microns; and iii) at least 90% of the particles have a volume diameter lower than 5.0 microns. Micronized formoterol fumarate dihydrate utilized in the formulation of the present invention is also advantageously characterized by a Specific Surface Area of 5 to 7.5 m$^2$/g, preferably 5.2 to 6.5 m$^2$/g, more preferably 5.5 to 5.8 m$^2$/g.

Both the micronized active ingredients utilized in the formulation of the present invention may be prepared by grinding in a suitable mill. Preferably they are prepared by grinding using a conventional fluid energy mill such as commercially available jet mill micronizers having grinding chambers of different diameters. Depending on the type of the apparatus and size of the batch, the person skilled in the art shall suitably adjust the milling parameters such as the operating pressure, the feeding rate and other operating conditions to achieve the desired particle size.

In particular, to achieve the claimed particle size distribution of BDP, it is highly advantageous to utilize a jet mill micronizer having a grinding chamber of a diameter of 300 mm.

In a preferred embodiment, the present invention is directed dry powder formulation for use in a dry powder inhaler (DPI) comprising:

(a) a fraction of fine particles made of a mixture composed of 98 percent by weight of particles of alpha-lactose monohydrate and 2 percent by weight of magnesium stearate, said mixture having a mass median diameter equal to or lower than 6 microns;

(b) a fraction of coarse particles constituted of alpha-lactose monohydrate having a mass diameter of 212 to 355 microns and the ratio between the fine particles and the coarse particles being 10:90 percent by weight; and (c) formoterol fumarate dihydrate in combination with beclometasone dipropionate (BDP) as active ingredients both in form of micronized particles; wherein i) no more than 10% of said BDP particles have a diameter [d(v,0.1)] lower than 0.7 microns, ii) no more than 50% of said particles have a diameter [d(v,0.5)] of 1.6 microns to 1.9 microns; and iii) at least 90% of said particles have a diameter lower than 4.0 microns.

The present invention is also directed to a process for preparing the dry powder formulation disclosed herein comprising the step of mixing the fraction of fine particles (a), the fraction of coarse particles (b) with both the micronized active ingredients.

The carrier particles comprising the fraction of fine particles and the fraction of coarse particles may be prepared by mixing in suitable apparatus known to the skilled person, for example a Turbula™ mixer. The two fractions are preferably mixed in a Turbula™ mixer operating at a rotation speed of 16 r.p.m. for a period of 30 to 300 minutes, preferably 150 to 240 minutes.

The mixture of the carrier particles with the active ingredient particles may be carried out by mixing the components in suitable apparatus known to the skilled person, such as Turbula™ mixer for a period sufficient to achieve the homogeneity of the active ingredient in the final mixture, preferably 30 to 120 minutes, more preferably 45 to 100 minutes.

Optionally, in an alternative embodiment, one active ingredient is first mixed with a portion of the carrier particles and the resulting blend is forced through a sieve, then, the further active ingredient and the remaining part of the carrier particles are blended with the sieved mixture; and finally the resulting mixture is sieved through a sieve, and mixed again.

The skilled person shall select the mesh size of the sieve depending on the particle size of the coarse particles.

The ratio between the carrier particles and the active ingredients will depend on the type of inhaler device used and the required dose.

Advantageously, the formulation of the invention may be suitable for delivering a therapeutic amount of both active ingredients in one or more actuations (shots or puffs) of the inhaler.

For example, the formulations will be suitable for delivering 6 to 12 μg formoterol (as fumarate dihydrate) per actuation, especially 6 μg or 12 μg per actuation, and 50 to 200 μg beclometasone dipropionate per actuation, especially 50, 100, or 200 μg per actuation.

The daily therapeutically effective dose may vary from 6 μg to 24 μg for formoterol and from 50 μg to 800 μg for BDP.

The dry powder formulation of the invention may be utilized with any dry powder inhaler.

Dry powder inhalers (DPIs) can be divided into two basic types:

(i) single dose inhalers, for the administration of single subdivided doses of the active compound; each single dose is usually filled in a capsule; and (ii) multidose inhalers pre-loaded with quantities of active principles sufficient for longer treatment cycles.

Said dry powder formulation is particularly suitable for multidose DPIs comprising a reservoir from which individual therapeutic dosages can be withdrawn on demand through actuation of the device, for example that described in WO 2004/012801, which is incorporated herein by reference in its entirety. Other multi-dose devices that may be used are for instance the DISKUS™ of GlaxoSmithKline, the TURBOHALER™ of AstraZeneca, TWISTHALER™ of Schering and CLICKHALER™ of Innovata. As marketed examples of single-dose devices, there may be mentioned ROTOHALER™ of GlaxoSmithKline and HANDIHALER™ of Boehringer Ingelheim.

In a preferred embodiment of the present invention, the dry powder formulation is filled in the DPI disclosed in WO 2004/012801, which is incorporated herein by reference in its entirety.

In case the ingress of moisture into the formulation is to be avoided, it may be desired to overwrap the DPI in a flexible package capable of resisting moisture ingress such as that disclosed in EP 1760008, which is incorporated herein by reference in its entirety.

Administration of the formulation of the present invention may be indicated for the prevention and/or treatment of a wide range of conditions including respiratory disorders such as chronic obstructive pulmonary disease (COPD) and asthma of all types and severity.

Other respiratory disorders characterized by obstruction of the peripheral airways as a result of inflammation and presence of mucus such as chronic obstructive bronchiolitis, and chronic bronchitis may also benefit by this kind of formulation.

Other features of the invention will become apparent in the course of the following descriptions of exemplary embodiments which are given for illustration of the invention and are not intended to be limiting thereof

EXAMPLES

Example 1

Preparation of Different Batches of Micronised Particles of Beclometasone Dipropionate Different batches of beclometasone dipropionate were milled in a jet mill micronizer MC JETMILL®300 (Jetpharma Sa, Switzerland) having a grinding chamber of a diameter of 300 mm. The micronized batches were characterized in terms of particle size distribution and Specific Surface Area.

The particle size was determined by laser diffraction using a Malvern apparatus. The parameter taken into consideration was the VD in microns of 10%, 50% and 90% of the particles expressed as d(v,0.1), d(v, 0.5) and d(v, 0.9), respectively, which correspond to the mass diameter assuming a size independent density for the particles. The span [d(v,0.9)−d(v, 0.1)]/d(v,0.5) is also reported. The Specific Surface Area (SSA) was determined by BET nitrogen adsorption using a Coulter SA3100 apparatus as a mean of three determinations. The relevant data are reported in Table 1.

TABLE 1

Particle size distribution and Specific Surface Area (SSA) of different batches of micronised beclometasone dipropionate.

| Particle size (μm) | Batch 1 | Batch 2 | Batch 3 | Batch 4 |
|---|---|---|---|---|
| d (v, 0.1) | 0.86 | 0.96 | 0.95 | 0.91 |
| d (v, 0.5) | 1.63 | 1.81 | 1.71 | 1.84 |
| d (v, 0.9) | 3.15 | 3.33 | 2.97 | 3.76 |

TABLE 1-continued

| Particle size distribution and Specific Surface Area (SSA) of different batches of micronised beclometasone dipropionate. | | | | |
|---|---|---|---|---|
| Particle size (μm) | Batch 1 | Batch 2 | Batch 3 | Batch 4 |
| Span | 1.41 | 1.31 | 1.19 | 1.54 |
| SSA ($m^2/g$) | 6.61 | 5.90 | 6.12 | 6.28 |

Example 2

Preparation of the Fraction of Fine Particles (a)

About 40 kg of co-micronized particles were prepared. Particles of α-lactose monohydrate having a particle size of less than 250 microns (Meggle D 30, Meggle), and magnesium stearate particles having a particle size of less than 35 microns in a ratio 98:2 percent by weight were co-micronized by milling in a jet mill operating under nitrogen to obtain the fraction of fine particles (a). At the end of the treatment, said co-micronized particles have a mass median diameter (MMD) of about 6 microns.

Example 3

Preparation of the "Carrier" (Fraction (a)+Fraction (b))

A sample of the fine particles of Example 1 were mixed with fissured coarse particles of α-lactose monohydrate having a mass diameter comprised between 212 and 355 microns, and obtained by sieving, in the ratio 90:10 percent by weight. The mixing was carried out in a Turbula mixer operating at a rotation speed of 16 r.p.m. for a period of 240 minutes. The resulting mixtures of particles, is termed hereinafter the "carrier".

Example 4

Preparation of the Dry Powder Formulation

A portion of the "carrier" as obtained in Example 3 was mixed with micronized formoterol fumarate dihydrate (FF) in a Turbula mixer for 30 minutes at 32 r.p.m., and the resulting blend was forced through a sieve with mesh size of 0.3 mm (300 microns). Micronized beclometasone dipropionate (BDP) batch 1 or 4 as obtained in Example 1 and the remaining part of the "carrier" were blended in a Turbula mixer for 60 minutes at 16 r.p.m. with the sieved mixture to obtain the final formulation.

The ratio of the active ingredients to 10 mg of the "carrier" is 6 microgram of FF dihydrate (theoretical delivered dose 4.5 microgram) and 100 microgram of BDP. The powder formulations were characterized in terms of aerosol performances after loading it in the multidose dry powder inhaler described in WO 2004/012801, which is incorporated herein by reference in its entirety.

The evaluation of the aerosol performance was carried out using the Andersen Cascade Impactor (ACI) according to the conditions reported in the European Pharmacopeia $6^{th}$ Ed 2008, par 2.9.18, pages 293-295, which is incorporated herein by reference in its entirety. After aerosolization of 3 doses, the ACI apparatus was disassembled and the amounts of drug deposited in the stages were recovered by washing with a solvent mixture and then quantified by High-Performance Liquid Chromatography (HPLC). The following parameters, were calculated: i) the delivered dose which is the amount of drug delivered from the device recovered in the impactor; ii) the fine particle mass (FPM) which is the amount of delivered dose having a particle size equal to or lower than 5.0 microns; iii) the fine particle fraction (FPF) which is the percentage of the fine particle dose; and iv) the MMAD. The results (mean value±S.D) are reported in Table 2.

TABLE 2

| Aerosol performances. | | |
|---|---|---|
| Sample | Batch 1 | Batch 4 |
| FF | | |
| Delivered Dose (μg) | 5.5 (±0.2) | 5.1 (±0.3) |
| Fine Particle Mass < 5 μm (μg) | 3.4 (±0.3) | 3.2 (±0.2) |
| Fine Particle Fraction < 5 μm (%) | 62.8 (±2.4) | 63.0 (±2.2) |
| Fine Particle Mass < 1 μm (μg) | 0.9 (±0.1) | 0.8 (±0.1) |
| Fine Particle Fraction < 1 μm (%) | 16.9 (±1.0) | 15.6 (±0.4) |
| MMAD (μm) | 1.69 (±0.0) | 1.75 (±0.0) |
| BDP | | |
| Delivered Dose (μg) | 89.8 (±3.7) | 88.2 (±3.5) |
| Fine Particle Mass (μg) | 54.0 (±4.0) | 52.4 (± 2.9) |
| Fine Particle Fraction (%) | 60.1 (±2.3) | 59.4 (±1.8) |
| Fine Particle Mass < 1 μm (μg) | 24.2 (±2.5) | 23.1 (±1.7) |
| Fine Particle Fraction < 1 μm (%) | 26.9 (±1.9) | 26.2 (±1.2) |
| MMAD (μm) | 1.23 (±0.1)[a] | 1.25 (±0.1)[a] |

[a]GSD which is the geometric standard deviation

From the data in Table 2, it can be appreciated that the formulations prepared using the micronized batches of BDP of Example 1 show a higher respirable fraction (FPF), for both the active ingredients (slightly more than 60%) than the corresponding pMDI formulation currently on the market (about 40%). They also give rise to a higher fraction of particles having a diameter equal or less than 1.1 microns (more than 25% for both the active ingredients).

Example 5

Therapeutic Equivalence of FF/BDP Dry Powder Formulation of the Invention with the Corresponding pMDI Formulation Currently on the Market The study was designed to show that FF/BDP dry powder formulation delivered via the DPI disclosed in WO 2004/012801, which is incorporated herein by reference in its entirety, is therapeutically equivalent to the corresponding pMDI formulation on the market.

Study Design:

A 5-way cross-over, double-blind, double-dummy clinical study. 69 asthmatic patients with $FEV_1$ 60% to 90% pred. were randomized. The 5 single doses tested were: 24/400 μg FF/BDP via DPI or pMDI, 6/100 μg FF/BDP via DPI or pMDI and placebo.

Primary Objective:

$FEV_1$ $AUC_{0-12h}$, which is the forced expiratory volume area under the curve for the time period 0 to 12 hours. FEV1 is the maximal amount of air that can be forcefully exhaled in one second.

Results

For $FEV_1AUC_{0-12h}$, non-inferiority between formulations was demonstrated with low dose and with high dose. Both doses were significantly better than placebo. Superiority of high dose versus low dose was shown for both formulations on $FEV_1AUC_{0-12h}$, reaching statistical significance for DPI. Safety and tolerability were good and comparable.

Example 6

Further Evidence of the Therapeutic Equivalence of FF/BDP Dry Powder Formulation of the Invention with the Corresponding pMDI Formulation Currently on the Market The aim of the study was to test the efficacy of 6/100 μg FF/BDP dry powder formulation delivered via the DPI (hereinafter FF/BDP DPI) disclosed in WO 2004/012801, which is incorporated herein by reference in its entirety, versus the same dose of the corresponding pMDI formulation on the market (hereinafter FF/BDP pMDI) and the 100 μg BDP DPI formulation on the market (Clenil Pulvinal®, hereinafter BDP DPI).

Study Design:

A phase III, 8-week, multinational, multicentre, randomized, double-blind, triple-dummy, active controlled, 3-arm parallel-group clinical trial was carried out in adult asthmatic patients. One inhalation twice daily of each formulation was administered for one month of treatment.

Primary Objective:

To demonstrate that FF/BDP DPI is non-inferior to FF/BDP pMDI in terms of change from baseline to the entire treatment period in average pre-dose morning peak expiratory flow (PEF). PEF is a person's maximum speed of expiration, as measured with a peak flow meter, a small, hand-held device used to monitor a person's ability to breathe out air. It measures the airflow through the bronchi and thus the degree of obstruction in the airways.

Secondary Objectives:

To evaluate the superiority of FF/BDP DPI over BDP DPI in terms of change from baseline to the entire treatment period in average pre-dose morning PEF. To evaluate the effect of FF/BDP DPI on other lung function parameters and on clinical outcome measures, and the safety and tolerability.

Results:

The non-inferiority of FF/BDP DPI relative to FF/BDP pMDI in terms of the primary efficacy variable has been demonstrated. The same results as for pre-dose morning PEF have been obtained for pre-dose evening PEF. No significant differences between treatments in terms of daily PEF variability have been observed. The superiority over BDP DPI of both FF/BDP DPI and FF/BDP pMDI has also been demonstrated. The FF/BDP DPI formulation turned out to be comparable to FF/BDP pMDI in terms of safety and tolerability.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A dry powder formulation for use in a dry powder inhaler, comprising:
   (a) a fraction of fine particles made of a mixture comprising 90 to 99.5 percent by weight of particles of a physiologically acceptable excipient and 0.5 to 10 percent by weight of magnesium stearate, said mixture having a mass median diameter lower than 20 microns;
   (b) a fraction of coarse particles comprising a physiologically acceptable excipient having a mass median diameter equal to or higher than 100 microns, wherein the weight ratio between said fine particles and said coarse particles is 1:99 to 30:70 percent by weight; and
   (c1) formoterol fumarate dihydrate in the form of micronized particles;
   (c2) beclometasone dipropionate (BDP) in the form of micronized particles;
   wherein: (i) no more than 10% of said BDP particles (c2) have a volume diameter lower than 0.6 microns; (ii) no more than 50% of said BDP particles (c2) have a volume diameter of 1.5 microns to 2.0 microns; and (iii) at least 90% of said BDP particles (c2) have a volume diameter lower than 4.7 microns,
   wherein said BDP particles (c2) are further characterized by a specific surface area of 5.5 to 7.0 m²/g.

2. A formulation according to claim 1, wherein said BDP particles (c2) have a d(v,0.1) of 0.8 to 1.0 microns, a d(v,0.5) of 1.5 to 2.0 microns, a d(v,0.9) of 2.5 to 4.7 microns, and a particle size span, defined as [d(v,0.9)−d(v,0.1)]/d(v,0.5) of 1.2 to 2.2.

3. A formulation according to claim 2, wherein said BDP particles (c2) have a particle size span of 1.3 to 2.1.

4. A formulation according to claim 1, wherein said BDP particles (c2) are further characterized by a specific surface area of 5.9 to 6.8 m²/g.

5. A formulation according to claim 1, wherein the weight ratio of fine particles (a) to coarse particles (b) is 2:98 to 20:80 percent by weight.

6. A formulation according to claim 5, wherein said weight ratio is 10:90 percent by weight.

7. A formulation according to claim 1, wherein said fraction of fine particles (a) has a mass median diameter equal to or lower than 10 microns.

8. A formulation according to claim 1, wherein said coarse particles (b) comprise alpha-lactose monohydrate.

9. A formulation according to claim 1, wherein said coarse particles (b) have a mass median diameter equal to or greater than 175 microns.

10. A formulation according to claim 9, wherein said mass median diameter is 212 to 355 microns.

11. A dry powder formulation for use in a dry powder inhaler, comprising:
   (a) a fraction of fine particles consisting of a mixture consisting of 98 percent by weight of particles of alpha-lactose monohydrate and 2 percent by weight of magnesium stearate, said mixture having a mass median diameter equal to or lower than 6 microns;
   (b) a fraction of coarse particles consisting of alpha-lactose monohydrate having a mass diameter of 212 to 355 microns, wherein the weight ratio between said fine particles and said coarse particles is 10:90 percent by weight; and
   (c1) formoterol fumarate dihydrate in the form of micronized particles;
   (c2) beclometasone dipropionate (BDP) in the form of micronized particles;
   wherein: (i) no more than 10% of said BDP particles (c2) have a volume diameter lower than 0.7 microns, (ii) no more than 50% of said BDP (c2) particles have a volume diameter of 1.6 microns to 1.9 microns; and (iii) at least 90% of said BDP particles (c2) have a volume diameter lower than 4.0 microns, wherein said BDP particles (c2) are further characterized by a specific surface area of 5.5 to 7.0 m²/g.

12. A dry powder inhaler filled with a dry powder formulation according to claim 1.

13. A method for the prevention and/or treatment of an inflammatory or obstructive airways disease, comprising administering an effective amount of a formulation according to claim 1 to a subject in need thereof.

14. A method according to claim 13, wherein said disease is asthma or chronic obstructive pulmonary disease.

15. A formulation according to claim 1, wherein said micronized particles of formoterol fumarate dehydrate (c1) have a diameter of less than 10 microns.

16. A formulation according to claim 1, wherein said micronized particles of formoterol fumarate dehydrate (c1) have a diameter of less than 6 microns.

17. A formulation according to claim 1, wherein at least 90% of said micronized particles of formoterol fumarate dehydrate (c1) have a volume diameter lower than 5.0 microns.

18. A formulation according to claim 1, wherein said micronized particles of formoterol fumarate dehydrate (c1) have a particle size distribution is such that:
  (i) no more than 10% of said particles have a volume diameter lower than 0.8 microns;
  (ii) no more than 50% of said particles have a volume diameter lower than 1.7 microns; and
  (iii) at least 90% of said particles have a volume diameter lower than 5.0 microns.

19. A formulation according to claim 1, wherein said micronized particles of formoterol fumarate dehydrate (c1) are characterized by a specific surface area of 5 to 7.5 m²/g.

20. A formulation according to claim 1, wherein said micronized particles of formoterol fumarate dihydrate (c1) are characterized by a specific surface area of 5.2 to 6.5 m²/g.

21. A formulation according to claim 1, wherein said micronized particles of formoterol fumarate dehydrate (c1) are characterized by a specific surface area of preferably 5.5 to 5.8 m²/g.

* * * * *